US011000082B2

(12) United States Patent
Lee et al.

(10) Patent No.: US 11,000,082 B2
(45) Date of Patent: May 11, 2021

(54) ASSISTIVE GLOVE FOR ARTIFICIAL HANDS

(71) Applicant: Purdue Research Foundation, West Lafayette, IN (US)

(72) Inventors: Chi Hwan Lee, West Lafayette, IN (US); Min Ku Kim, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 449 days.

(21) Appl. No.: 15/902,039

(22) Filed: Feb. 22, 2018

(65) Prior Publication Data

US 2018/0235293 A1 Aug. 23, 2018

Related U.S. Application Data

(60) Provisional application No. 62/462,330, filed on Feb. 22, 2017.

(51) Int. Cl.
| | |
|---|---|
| *A61F 2/58* | (2006.01) |
| *A41D 19/00* | (2006.01) |
| *A41D 1/00* | (2018.01) |
| *A41D 31/00* | (2019.01) |
| *B32B 1/00* | (2006.01) |
| *B32B 25/14* | (2006.01) |
| *G01L 1/20* | (2006.01) |
| *G01L 1/22* | (2006.01) |
| *A61F 2/76* | (2006.01) |
| *A61F 2/50* | (2006.01) |
| *G01K 7/16* | (2006.01) |
| *G01N 27/22* | (2006.01) |

(52) U.S. Cl.
CPC ......... *A41D 19/0027* (2013.01); *A41D 1/002* (2013.01); *A41D 1/005* (2013.01); *A41D 19/0006* (2013.01); *A41D 19/0058* (2013.01); *A41D 19/0082* (2013.01); *A41D 31/00* (2013.01); *A61F 2/583* (2013.01); *A61F 2/76* (2013.01); *B32B 1/00* (2013.01); *B32B 25/14* (2013.01); *G01L 1/205* (2013.01); *G01L 1/2287* (2013.01); *A41D 2500/50* (2013.01); *A61F 2002/5001* (2013.01); *A61F 2002/5058* (2013.01); *A61F 2002/5063* (2013.01); *A61F 2002/7615* (2013.01); *B32B 2437/02* (2013.01); *G01K 7/16* (2013.01); *G01N 27/223* (2013.01)

(58) Field of Classification Search
CPC .............. A41D 19/0027; A41D 19/006; A41D 19/0058; A41D 19/0082; A41D 1/002; A41D 1/005; A61D 31/00; A61F 2/583; A61F 2/76; B32B 1/00; B32B 25/14
USPC .......................................................... 623/57
See application file for complete search history.

(56) References Cited

U.S. PATENT DOCUMENTS

| | | | |
|---|---|---|---|
| 2012/0029399 A1* | 2/2012 | Sankai | A61H 1/0288 601/40 |
| 2014/0277588 A1* | 9/2014 | Patt | A61F 2/586 623/57 |

(Continued)

*Primary Examiner* — Suba Ganesan
*Assistant Examiner* — Aren Patel
(74) *Attorney, Agent, or Firm* — Hartman Global IP Law; Gary M. Hartman; Domenica N.S. Hartman

(57) ABSTRACT

Electronic assistive gloves for covering artificial prosthetic or robotic hands. The glove includes a base layer formed to fit on the artificial hand, a plurality of sensors carried by the base layer, and an encapsulation layer covering the base layer and formed of a material that mimics human skin.

20 Claims, 12 Drawing Sheets

(56) References Cited

U.S. PATENT DOCUMENTS

| | | | |
|---|---|---|---|
| 2016/0033343 A1* | 2/2016 | Park | G01L 1/146 |
| | | | 73/862.046 |
| 2016/0250015 A1* | 9/2016 | Kim | G01L 5/228 |
| | | | 623/15.12 |
| 2017/0270331 A1* | 9/2017 | Hoeink | G06K 7/10891 |

* cited by examiner

ASSISTIVE GLOVE FOR ARTIFICIAL HANDS

CROSS REFERENCE TO RELATED APPLICATIONS

This application claims the benefit of U.S. Provisional Application No. 62/462,330, filed Feb. 22, 2017, the contents of which are incorporated herein by reference.

BACKGROUND OF THE INVENTION

The present invention generally relates to assistive devices, and particularly electronic assistive gloves for covering artificial prosthetic or robotic hands.

A significant challenge exists in artificial hands for assistive robotics and prosthetics to establish appropriate social interactions and create emotional connections in the society. Social interactions are strongly associated with physical touch such as a handshake, gentle stroke, pat, and even high-five, justifying considerable investment in technology to duplicate a humanlike appearance, softness, and somatosensory functions of artificial hands. For this purpose, modern artificial hands are blanketed around with electronic skin (e-skin) that includes functional sensors built on a soft elastomeric substrate not only to perceive environmental stimuli but also to provide mechanical softness. Nonetheless, a key challenge still remains in the ability to seamlessly integrate e-skins with existing artificial hands due to the geometric complexity of hands, almost invariably resulting in poor mechanical and electrical coupling. Thus, improvements are needed in the field.

BRIEF DESCRIPTION OF THE INVENTION

The present invention provides electronic assistive gloves for use with artificial prosthetic or robotic hands.

According to one aspect of the invention, an electronic assistive glove for covering an artificial hand includes a base layer formed to fit on the artificial hand, a plurality of sensors carried by the base layer, and an encapsulation layer covering the base layer and formed of a material that mimics human skin.

Technical aspects of a glove as described above preferably include the ability to incorporate a variety of sensors into the glove to provide somatosensory functions to an artificial hand, yet achieve the ability of the glove to resemble an actual human hand.

Other aspects and advantages of this invention will be further appreciated from the following detailed description.

DETAILED DESCRIPTION OF THE INVENTION

Figure 1:
FIG. 1 is an image showing three nonlimiting examples of electronic assistive gloves (e-gloves) for use with artificial prosthetic or robotic hands in accordance with nonlimiting embodiments of the present invention.

Throughout this description, some aspects are described in terms that would ordinarily be implemented as software programs. Those skilled in the art will readily recognize that the equivalent of such software can also be constructed in hardware, firmware, or micro-code. Because data-manipulation algorithms and systems are well known, the present description is directed in particular to algorithms and systems forming part of, or cooperating more directly with, systems and methods shown in the drawings and, as such, particularly described herein. Other aspects of such algorithms and systems, and hardware or software for producing and otherwise processing signals or data involved therewith, not specifically shown or described herein, may be selected from such systems, algorithms, components, and elements known in the art. Given the systems and methods as described herein, software not specifically shown, suggested, or described herein that is useful for implementation of any aspect is conventional and within the ordinary skill in such arts.

The present disclosure provides electronic assistive gloves for use with artificial prosthetic or robotic hands in accordance with nonlimiting embodiments of the present invention. Such gloves, referred to herein as e-gloves, provide humanlike characteristics and are configured or adaptable to fit onto various types of artificial prosthetic and robotic hands (hereinafter, artificial hands). Exemplary e-gloves shown in FIG. 1 each comprise an encapsulation layer that forms an exterior glove that serves and is visible as the exterior surface of the e-gloves. The encapsulation layer of each e-glove surrounds and preferably completely covers a base layer shown in FIG. 3.

Figure 2:
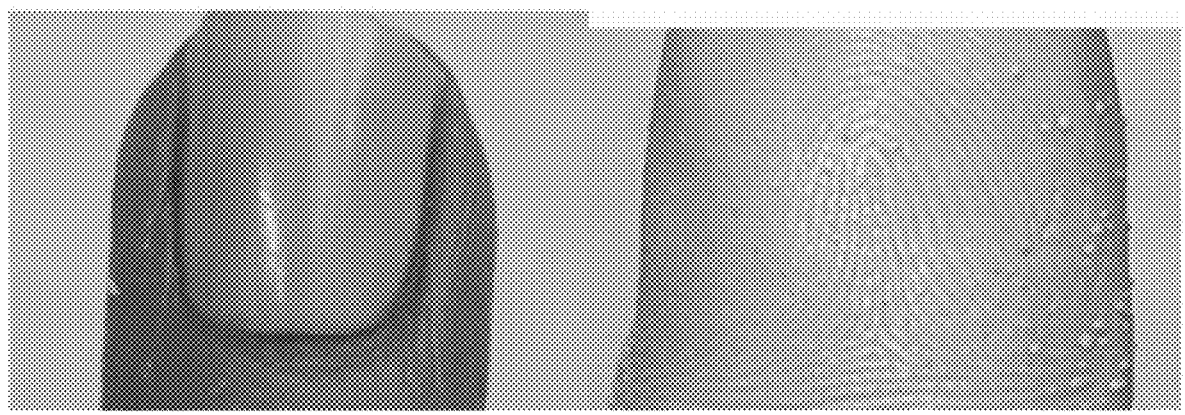
FIG. 2 contains images showing a fingernail and a fingerprint that form part of an exterior encapsulation layer of one of the e-gloves of FIG. 1, and demonstrates an extreme likeness to an actual human fingernail and fingerprint.

The e-gloves represented in FIG. 1 and details of one of the e-gloves shown in FIG. 2 demonstrate the humanlike appearance possible with preferred e-gloves of the present invention. Preferred characteristics of materials for the encapsulation layer include the ability to mimic human skin, which as used herein refers to characteristics with respect to one or more (though preferably all) of the following: color, texture, warmth, and mechanical properties. A preferred but nonlimiting example of a suitable material for the encapsulation layer is a silicone elastomer whose composition can be tailored to imitate various human skin tones and shapes. A particular example of such a silicone material is commercially available from Smooth-On, Inc., under the name ECOFLEX™.

Figure 3:
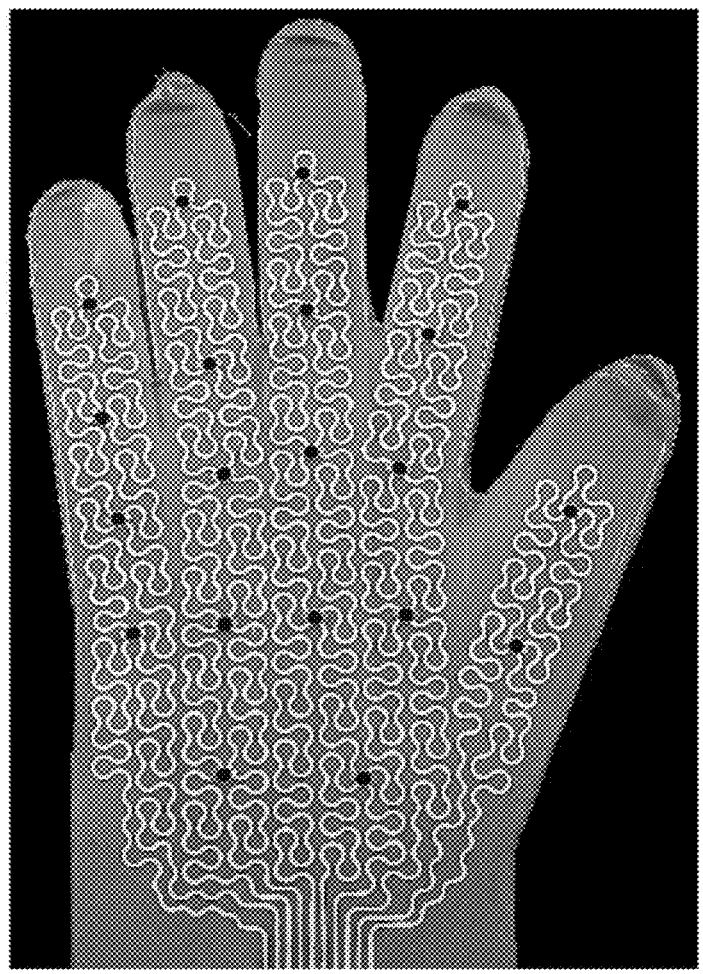
FIG. 3 is an image of a nonlimiting example of an interior base layer covered and completely concealed by the encapsulation layer of each e-glove of FIG. 1.

As evident from FIG. 1, the base layer of FIG. 3 is capable of being covered and completely concealed by the encapsulation layer and glove of an e-glove. In contrast to the encapsulation layer, whose role is to imitate the appearance of human skin and various features and characteristics associated with human skin (for example, the fingernail and finger print shown in FIG. 2), the role of the base layer is to imitate certain functional capabilities of human skin, for example, the ability to sense pressure or moisture, generate a surface temperature approximating normal hand temperatures (e.g., from about 34 to about 39° C.), etc. In the embodiment of FIG. 3, the base layer is fabricated to have a substrate formed of a flexible and preferably elastic material, as a nonlimiting example, nitrile rubber. The base layer forms an interior glove (hereinafter base glove) whose interior shape and size enable the e-glove to be donned on an artificial hand, and whose exterior shape and size are chosen so that, after the application of the encapsulation layer to the base layer, the resulting e-glove will have a desired shape and size.

Figure 4:
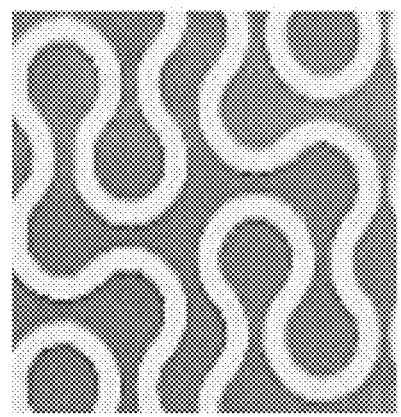
FIG. 4 is an inset image of the base layer of FIG. 3 and shows serpentine patterns of conductive traces on the surface of the base layer that interconnect sensors located on the base layer.

The base glove shown in FIG. 3 is represented as having a pattern of conductive traces on a least one of its surfaces, preferably at least the surface that will be located at the palm of the artificial hand on which the e-glove is installed. The conductive traces may be screen-printed onto the substrate of the base layer, for example, by screen-printing a flexible silver conductive ink on the substrate. FIG. 4 shows a detail of a portion of two adjacent conductive traces on the substrate of the base layer. As evident from FIG. 3, the conductive traces are in the form of serpentine patterns to define individual serpentine trace patterns, each of which defines a path that starts adjacent a wrist region of the base glove, has an outbound portion routed to a location adjacent the tip of one of the fingers of the base glove, and an inbound portion that is routed back to form a terminus of the path at the wrist region of the base glove. The start and terminus of each path defines leads for one of the individual serpentine trace patterns at the wrist region of the base glove. The individual serpentine trace patterns preferably are electrically isolated from each other by the substrate of the base glove. The serpentine shapes of the trace patterns are intended to promote the stretchability and flexibility of the e-glove.

FIG. 3 also shows sensors located within each serpentine trace pattern, bridging and connected to the outbound and inbound portions of each serpentine trace pattern. The base glove of FIG. 3 comprises multiple sensors located within a portion of each serpentine trace pattern located on one of the fingers of the base glove, and multiple sensors located within a portion of each serpentine trace pattern located within the palm of the base glove. The sensors provide a somatosensory function which outputs sensory information to the user or an electronic control and display unit (discussed in reference to FIG. 6). The sensors may be a single type of sensor or a combination of various types of sensors, including but not limited to temperature sensors, pressure sensors, and hydration sensors. Though shown as exclusively formed on the exterior surface of the base glove, the conductive traces and their associated pressure sensors could instead or additionally be provided on the interior surface of the encapsulation layer, or embedded into the encapsulation and/or base layers. In any event, the encapsulation layer cover and conceal the base layer, the serpentine trace pattern, and the sensors to ensure that the e-glove resembles an actual human hand.

Though various techniques may be employed to place sensors within each serpentine trace pattern, a nonlimiting example is as follows: A thin layer of sensor arrays is first fabricated in a silicon wafer with a chemically etchable sacrificial layer such as Poly(methyl methacrylate) (PMMA) by using a photolithographic process. The wafer is then soaked in acetone at room temperature until the sacrificial layer is completely dissolved. The resulting thin layer of sensor arrays remaining on the silicon wafer is substantially dried in air for around 3 minutes. The thin layer of sensor arrays is then picked up by using a water solution tape and printed onto the surface of a base glove substrate by applying a elastomeric polymer such as polydimethylsiloxane (PDMS), ECOFLEX™, or a silicone elastomer commercially available from Bluestar Silicones under the name SILBIONE®, as an adhesive layer.

Figure 5:
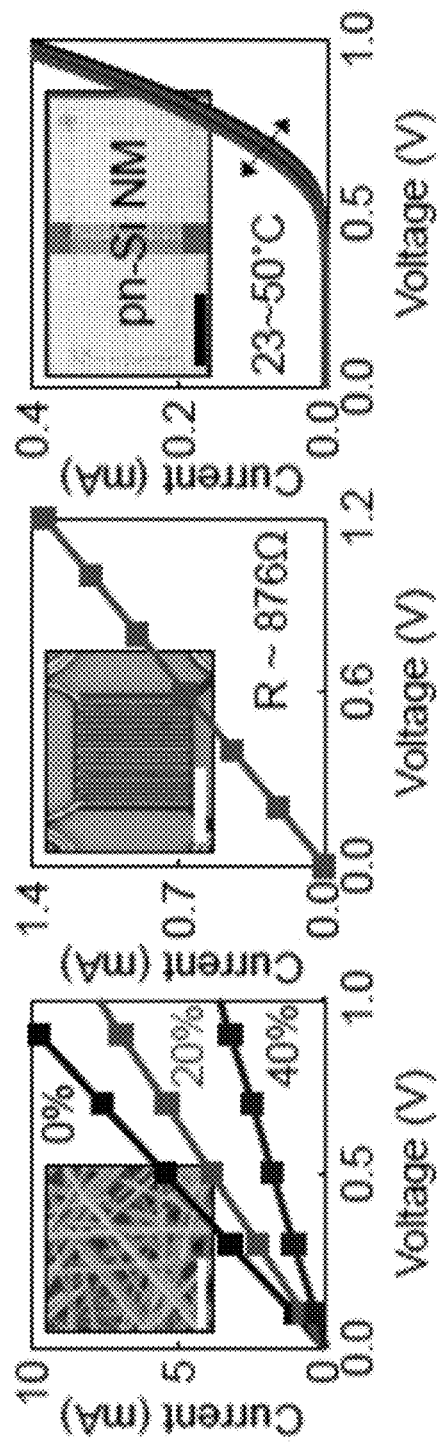
FIG. 5 contains three graphs characterizing performance characteristics of three different types of sensors that may be utilized with e-gloves in accordance with nonlimiting embodiments of the present invention.

FIG. 5 contains three graphs showing performance characteristics of three different but nonlimiting types of sensors that may be utilized in an e-glove within the scope of the present invention. Each graph plots current versus voltage (resistance) measurements of the sensor. The lefthand image plots strain characteristics for a sensor constructed of silver nanowire mesh elements (see inset) at various strain levels to characterize the device for its function as a pressure or strain sensor. The center graph plots temperature characteristics for an ultra-thin gold/polyimide passive temperature sensor (see inset) fabricated using standard photolithographic methods. The righthand graph plots temperature characteristics for a PIN diode active temperature sensor (see inset). The center and righthand graphs plot the temperature characteristics of the temperature sensors at various temperature to characterize the devices for their function as temperature sensors. All three types of sensors can be incorporated into an e-glove with separate serpentine trace patterns similar to that depicted in FIGS. 3 and 4.

FIG. 6(a) shows an e-glove placed on a prosthetic arm and electrically connected to an electronic control and display unit mounted to the prosthetic arm as a user interface for the e-glove. The electronic control and display unit is housed in a case. FIG. 6(b) is a detailed image of the electronic control and display unit, and shows a screen of the unit displaying the current temperature of the e-glove and a target temperature of one or more heating elements that are controlled with buttons located beneath the screen. The heating elements can be configured and fabricated on the interior surface of the encapsulation layer or on the exterior surface of the base glove in a similar manner to the serpentine trace patterns depicted in FIGS. 3 and 4. Alternatively, heating elements may be incorporated or otherwise embedded into the encapsulation or base layers of the encapsulation or base glove. FIG. 6(c) is an image of an electronic temperature control circuit of the unit that is fabricated on a flexible polyimide substrate and housed within the case of the electronic control and display unit.

Figure 6:
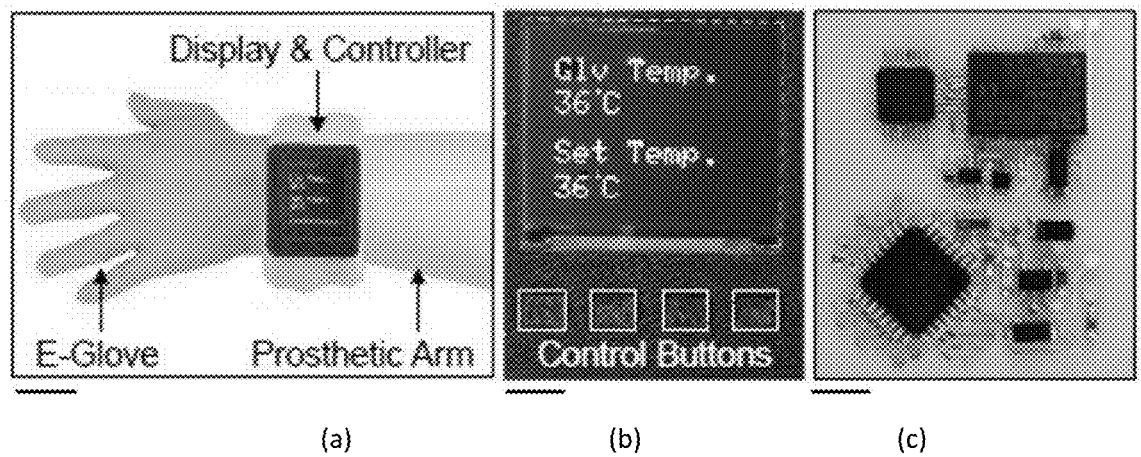
FIG. 6 contains images showing an e-glove placed on a prosthetic arm and connected to an electronic control and display unit for demonstrating a temperature stimulation capability using heating elements distributed within the e-glove.

The heating elements of the e-glove represented in FIG. 6 enable the wearer to control the temperature of an artificial hand with the electronic control and display unit located in close proximity to the hand. For this purpose, the electronic control and display unit must be electrically connected to the heating element(s), for example, through leads of the type shown on the base glove in FIG. 3. An e-glove equipped with sensors adapted to sense pressure, moisture, temperature, etc., can be similarly equipped with an electronic control and display unit located in close proximity to the artificial hand on which the e-glove is worn. Alternatively, the sensors may be equipped to communicate wirelessly with a remote electronic control and display unit, including a unit worn elsewhere on the wearer's body. Generally, the electronic control and display unit receives output signals from the sensors of the e-glove, optionally processes the signals to determine the output levels of the sensors, and displays the output levels or information derived therefrom to the wearer. The wearer may then take any appropriate action prompted by the output, for example, move the artificial hand to release or increase a grip, remove the hand from a hot surface, etc.

Figure 7:
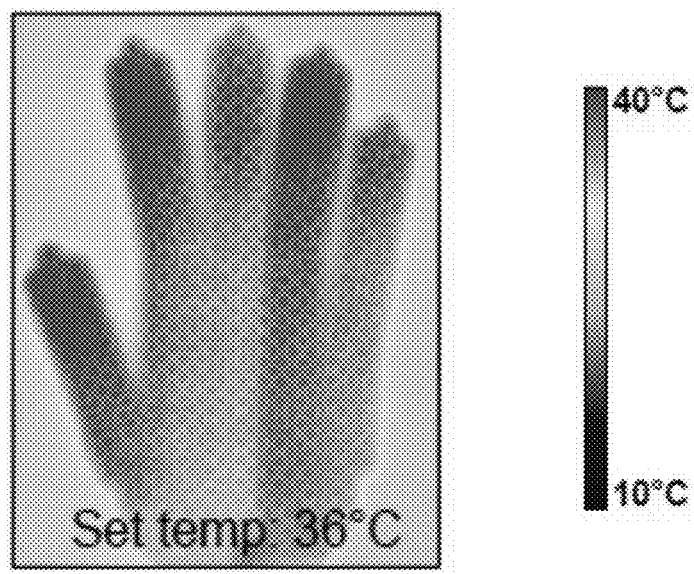
FIG. 7 contains an infrared (IR) image of an e-glove in which heating elements distributed within the e-glove have been activated.

An e-glove equipped with a heating element to provide a temperature stimulation capability as described in reference to FIG. 6 is desirable to promote the human characteristics of the e-glove by imitating the warmth of a human hand. FIG. 7 contains an infrared (IR) image of an e-glove equipped with a heating element that has been activated, and evidences a substantially uniform temperature of about 36° C. across the exterior surface of the e-glove.

Figure 8:
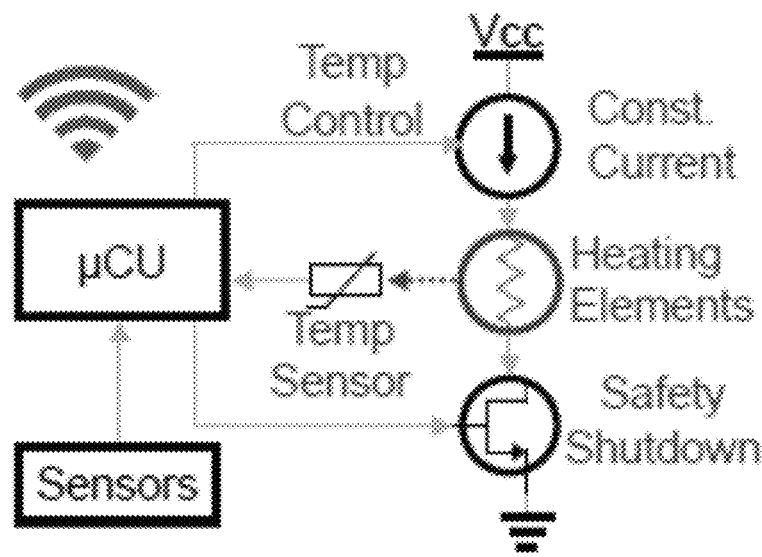
FIG. 8 is a schematic diagram of the electronic temperature control circuit of FIG. 6(c) for controlling the temperature of the e-glove of FIGS. 6 and 7.
Figure 9:
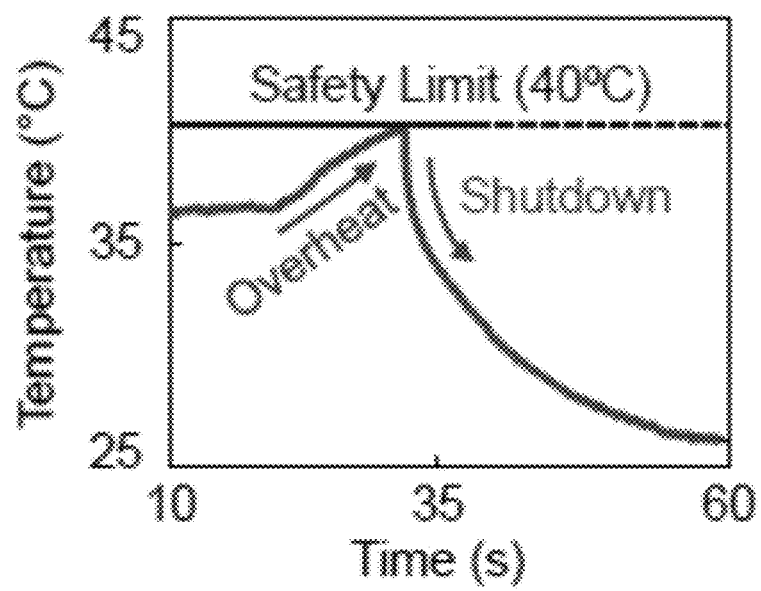
FIG. 9 is a graph demonstrating the operation of a safety shutdown system of the e-glove of FIGS. 6 through 8.

FIG. 8 is a schematic diagram of the electronic temperature control circuit of FIG. 6(c) for controlling the temperature of the e-glove of FIGS. 6(a) and 7. The control circuit uses a feedback system by collecting thermal data from temperature sensors on the e-glove, for example, incorporated in a manner similar to the serpentine trace patterns depicted in FIGS. 3 and 4. The control circuit also includes a safety shutdown system that, in case of overheating, employs transistor switches to disconnect the heating elements from a power source (Vcc) to prevent injury to the wearer or damage to the e-glove. FIG. 9 is a demonstration of the safety shutdown system, where the temperature of a heating element continues to rise until a safety limit of 40° C. was reached, at which point the control circuit detected an overheating condition and disconnected the heating element from its power source.

Figure 10:
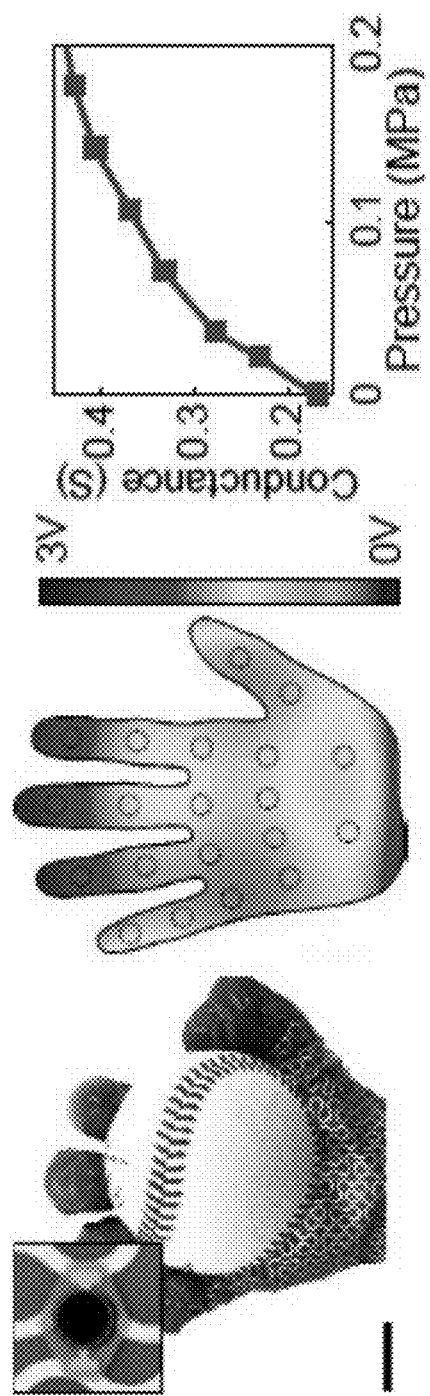
FIG. 10 contains images demonstrating a tactile sensation measurement capability of an e-glove using an array of pressure sensors distributed within the e-glove.

FIG. 10 represents an e-glove equipped with pressure sensors to provide a tactile sensation measurement capability. Suitable pressure sensors can be incorporated into an e-glove as described in reference to FIGS. 3 and 4, as well as the temperature sensors discussed in reference to FIGS. 6 through 9. In particular, the center image of FIG. 10 shows the e-glove as comprising an array of twenty pressure sensors distributed throughout the palm and fingers the e-glove similar to what is shown in FIG. 3. The lefthand image of FIG. 10 contains an inset showing a detailed view of a single pressure sensor connected to a serpentine trace pattern on the exterior surface of a base glove. The sensors are fabricated on polyimide substrates using copper patterns for connection to the serpentine trace pattern. In the embodiment shown in FIG. 10, the sensor uses a piezoresistive material as the pressure sensing element (black disk at the center of the sensor). The center image of FIG. 10 shows pressure data generated by a hand wearing the e-glove while grabbing a baseball as shown in the lefthand image of FIG. 10. The graph in FIG. 10 is a fitted representation of measurements acquired with the twenty pressure sensors of the e-glove, and serves as a characterization curve of conductance versus pressure such that the resistive loads of the pressure sensors can be translated to quantifiable pressure.

Figure 11:
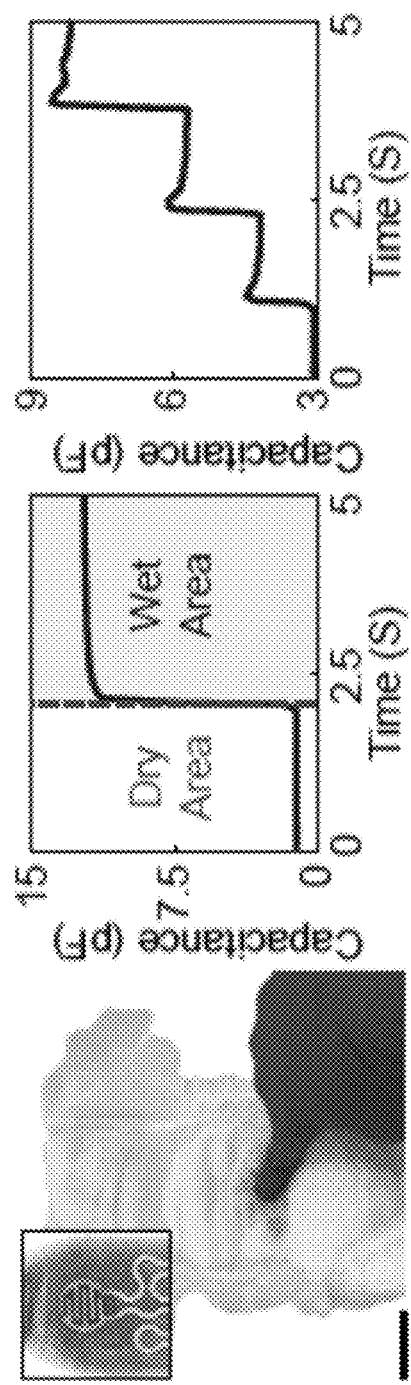
FIG. 11 contains images demonstrating a hydration sensing capability of an e-glove using an array of hydration sensors distributed within the e-glove.

FIG. 11 represents an e-glove equipped with hydration sensors to provide a hydration sensing capability for the e-glove. The lefthand image shows the e-glove grasping a wet diaper for the purpose of measuring the hydration levels of the diaper. The inset in the lefthand image of FIG. 11 shows a capacitive hydration sensor element located on the exterior of the e-glove. The center image of FIG. 11 contains a graph plotting measurements indicating a sharp change in capacitance when dry and wet regions of a diaper are grasped. The righthand image of FIG. 11 is a graph containing a characterization curve of the capacitive hydration sensor element.

Figure 12:
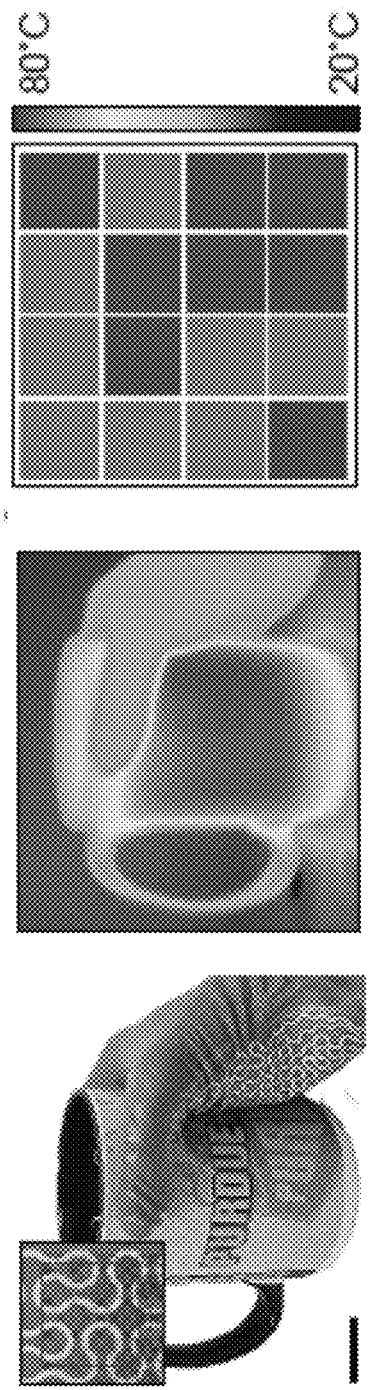
FIG. 12 contains images demonstrating temperature sensing characteristics of an e-glove equipped with an array of temperature sensors distributed within the e-glove.

FIG. 12 contains images demonstrating temperature sensing characteristics of an e-glove equipped with a 4×4 array of temperature sensors. An inset image in the lefthand image of FIG. 12 shows a portion of the temperature sensor array located on the e-glove. The lefthand image of FIG. 12 shows the e-glove holding a cup filled with hot water. The center image of FIG. 12 is an IR image of the cup shown in the lefthand image, and the righthand image is a representation of temperature measurements obtained with the temperature sensors of the e-glove.

Figure 13:
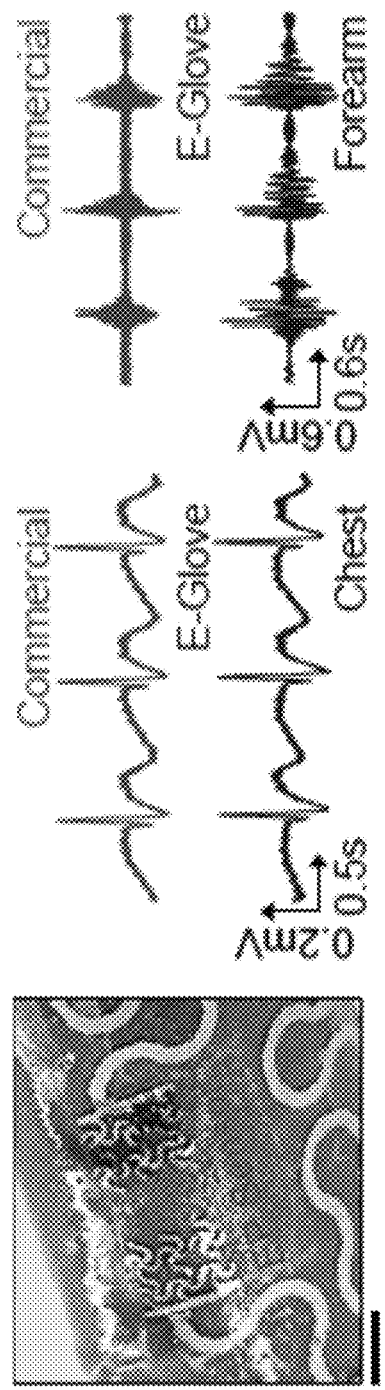
FIG. 13 contains images demonstrating the capability of an e-glove equipped with appropriate sensors to measure electrophysiological signals.

FIG. 13 contains images demonstrating the capability of an e-glove equipped with appropriate sensors to measure electrophysiological signals. The sensors were differential pairs of silver nanowire mesh sensors located on the exterior surface of the e-glove and configured as shown in the lefthand image of FIG. 13. Such sensors are capable of measuring the electrocardiogram (ECG) and electromyogram (EMG) signals by placing the e-glove in contact with regions of the body. As nonlimiting examples, the center and righthand images of FIG. 13 are graphs comparing electrophysiological signals measurements obtained with the e-glove to measurements obtained a commercially available sensor electrode when both were placed on the chest (center image) and forearm (righthand image) of an individual. The noise to signal level and performance were very comparable.

Figure 14:
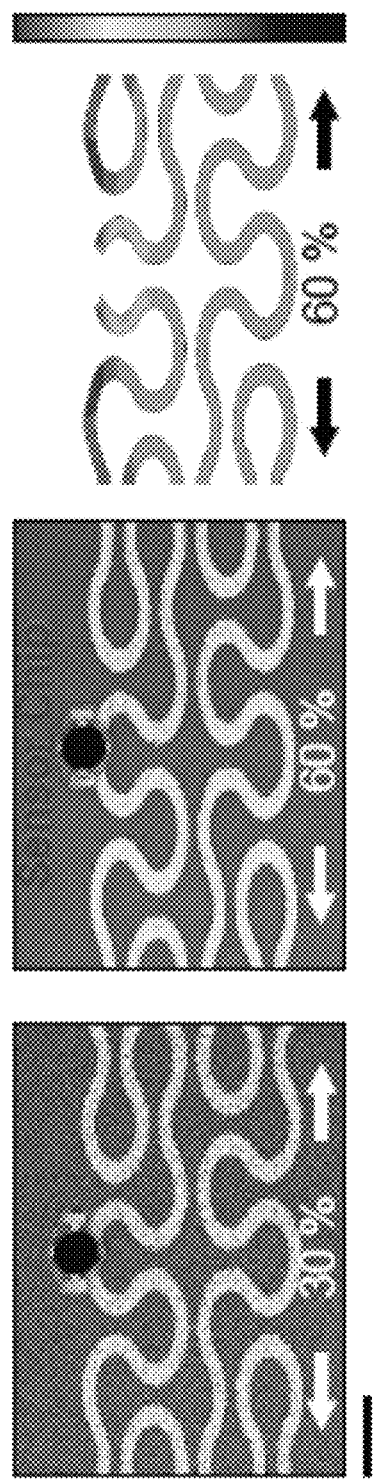
FIG. 14 contains images showing a serpentine trace pattern forming a connection layer and heating elements attached thereto, wherein the lefthand and center images depict one-dimensional strains induced on the serpentine trace pattern and the righthand image is a finite element analysis (FEA) verifying the experimental results of the lefthand and center images.

FIG. 14 contains images showing a serpentine trace pattern forming a connection layer and having a heating element attached. The lefthand and center images of FIG. 14 depict one-dimensional strain induced on the connection layer and heating element at 30% and 60% strain levels, demonstrating the capability of the serpentine trace pattern to withstand significant levels of strain without damage. The righthand image of FIG. 14 is a finite element analysis (FEA) verifying the experimental results of the lefthand and center images of FIG. 14.

Figure 15:
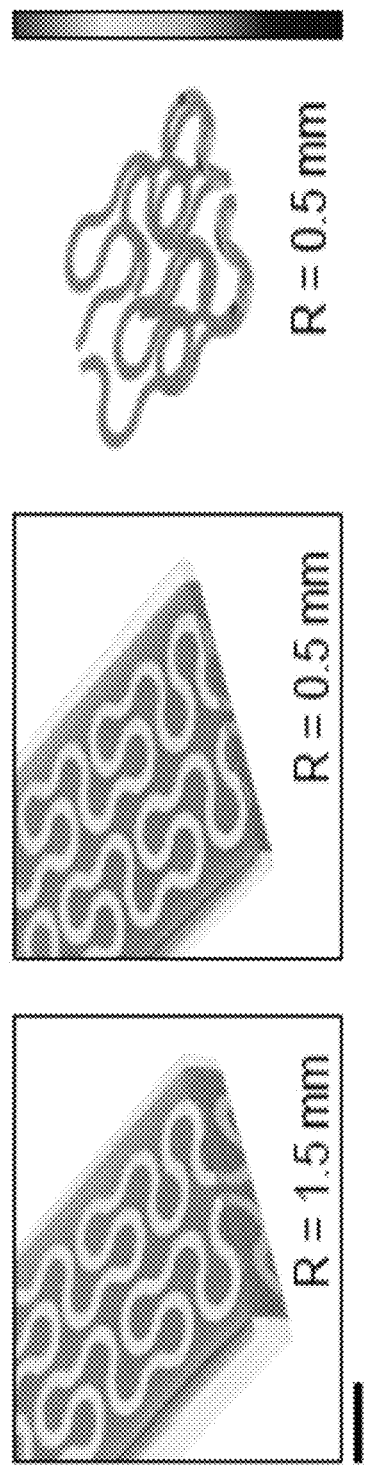
FIG. 15 contains lefthand and center images showing a serpentine trace pattern under different bending conditions, and a finite element model (FEM) verifying the experimental results of the lefthand and center images.

FIG. 15 contains lefthand and center images showing a serpentine trace pattern under different bending conditions (with the bending radii indicated in each image). The righthand image of FIG. 15 is a finite element model (FEM) verifying the experimental results of the lefthand and center images. FIG. 15 demonstrates the capability of the serpentine trace pattern to withstand significant bending without damage.

Figure 16:
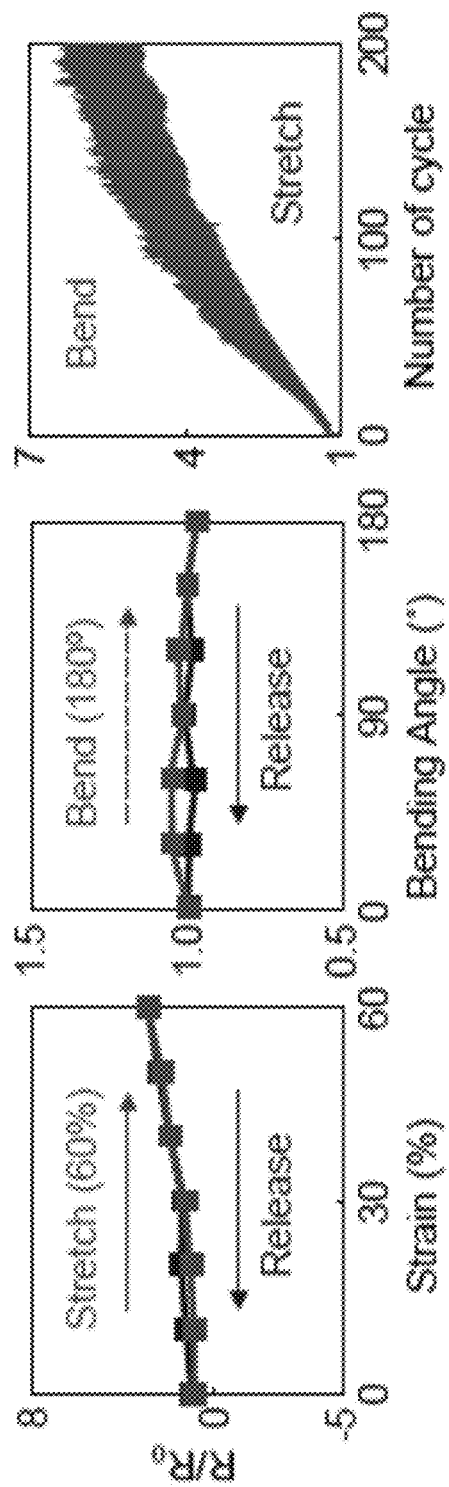
FIG. 16 contains graphs plotting data obtained under the conditions shown in FIGS. 14 and 15.

FIG. 16 contains graphs plotting data obtained under the conditions shown in FIGS. 14 and 15. The lefthand image of FIG. 16 is a plot of the change in resistance as one dimensional strain in the serpentine trace pattern was increased strain from 0 to 60%, and the center image of FIG. 16 is a plot of the change in resistance as bending of the serpentine trace pattern was increased from 0° to 180°. The righthand image of FIG. 16 is a graph plotting the change of resistance measurement during repeated stretching over 200 cycles. FIG. 16 reaffirms the capability of the serpentine trace pattern to withstand significant distortion without damage.

The invention is inclusive of combinations of the aspects described herein. References to a particular aspect, embodiment, version, and the like refer to features that are present in at least one aspect of the invention. Separate references to "an aspect" (or "embodiment") or "particular aspects" or the like do not necessarily refer to the same aspect or aspects; however, such aspects are not mutually exclusive, unless otherwise explicitly noted. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected within the spirit and scope of the invention.

The invention claimed is:

1. An electronic assistive glove for covering an artificial hand, the glove comprising:
    a base layer formed to fit on the artificial hand;
    a plurality of sensors carried by the base layer;
    conductive traces carried by the base layer and interconnecting the sensors, the conductive traces comprising individual trace patterns having serpentine shapes; and
    an encapsulation layer that conceals the base layer and the conductive traces, the encapsulation layer being formed of a material that mimics human skin.

2. The electronic assistive glove according to claim 1, wherein the glove comprises a palm and fingers extending from the palm, the sensors are arranged in different sets of the sensors that are each connected by one of the individual trace patterns of the conductive traces, some of the sensors of a first set of the different sets being located in the palm and connected by a first of the individual trace patterns to others of the sensors of the first set located in one of the fingers of the glove.

3. The electronic assistive glove according to claim 1, wherein the conductive traces are formed on the base layer, formed on the encapsulation layer, or embedded in the base or encapsulation layers.

4. The electronic assistive glove according to claim 1, wherein the base layer defines a base glove having a wrist region, fingers, and a palm therebetween, and each of the individual trace patterns defines a path that starts adjacent the wrist region of the base glove, has an outbound portion routed to a location adjacent a tip of one of the fingers of the base glove, and an inbound portion that is routed back to form a terminus of the path at the wrist region of the base glove.

5. The electronic assistive glove according to claim 4, wherein the start and terminus of each path defines electrical leads for a corresponding one of the individual trace patterns at the wrist region of the base glove.

6. The electronic assistive glove according to claim 4, wherein the individual trace patterns are electrically isolated from each other by the base layer.

7. The electronic assistive glove according to claim 4, wherein at least one of the sensors is located within a corresponding one of the individual trace patterns and bridges and is connected to the outbound and inbound portions of the corresponding individual trace pattern.

8. The electronic assistive glove according to claim 4, wherein the base glove comprises a plurality of the sensors located within a finger portion of each of the individual trace patterns located on the fingers of the base glove.

9. The electronic assistive glove according to claim 8, wherein the base glove comprises a plurality of the sensors located within a palm portion of each of the individual trace patterns located on the palm of the base glove.

10. The electronic assistive glove according to claim 1, wherein the sensors comprise a plurality of pressure sensors.

11. The electronic assistive glove according to claim 1, wherein the sensors comprise a plurality of temperature sensors.

12. The electronic assistive glove according to claim 1, wherein the sensors comprise a plurality of hydration sensors that measure hydration levels of objects grasped by the glove.

13. The electronic assistive glove according to claim 1, further comprising at least one heating element configured to maintain an exterior surface of the electronic assistive glove at a temperature of about 34 to about 39° C.

14. The electronic assistive glove according to claim 1, further comprising an electronic control and display unit that receives output signals from the sensors and displays information derived from the output signals.

15. The electronic assistive glove according to claim 14, wherein each of the individual trace patterns is connected to the electronic control and display unit.

16. The electronic assistive glove according to claim 1, wherein the sensors are added to the base layer by transfer printing.

17. The robotic hand covered by the electronic assistive glove according to claim 16.

18. The electronic assistive glove according to claim 1, wherein the artificial hand is a prosthetic hand.

19. The prosthetic hand covered by the electronic assistive glove according to claim 18.

20. The electronic assistive glove according to claim 1, wherein the artificial hand is a robotic hand.

* * * * *